US006186981B1

(12) United States Patent
Cho

(10) Patent No.: US 6,186,981 B1
(45) Date of Patent: Feb. 13, 2001

(54) CAVO-ATRIAL CANNULA

(76) Inventor: Peter Cho, 629 Budleigh Cir., Timonium, MD (US) 21093

( * ) Notice: Under 35 U.S.C. 154(b), the term of this patent shall be extended for 0 days.

(21) Appl. No.: 09/274,588

(22) Filed: Mar. 23, 1999

(51) Int. Cl.$^7$ .................................................. A61M 5/00
(52) U.S. Cl. ............................................................ 604/117
(58) Field of Search .................................. 604/264, 523, 604/528, 529, 532, 530, 164, 117

(56) References Cited

U.S. PATENT DOCUMENTS

| | | | |
|---|---|---|---|
| 3,920,023 | * 11/1975 | Dye et al. | 128/347 |
| 4,129,129 | 12/1978 | Amrine | 604/49 |
| 4,248,224 | 2/1981 | Jones | 128/214 |
| 4,309,994 | * 1/1982 | Grunwald | 128/214 |
| 4,581,390 | * 4/1986 | Flynn | 523/112 |
| 4,639,252 | 1/1987 | Kelley et al. | 604/282 |
| 4,747,840 | * 5/1988 | Ladika et al. | 604/281 |
| 4,804,359 | 2/1989 | Grunwald et al. | 604/4 |
| 5,021,043 | * 6/1991 | Becker et al. | 604/49 |
| 5,330,433 | 7/1994 | Fonger et al. | 604/164 |
| 5,354,263 | * 10/1994 | Coll | 604/8 |
| 5,478,309 | * 12/1995 | Sweezer et al. | 604/4 |
| 5,762,636 | * 6/1998 | Rupp et al. | 604/264 |
| 5,769,828 | 6/1998 | Jonkman | 604/280 |
| 5,921,978 | * 7/1999 | Thompson et al. | 604/529 |
| 5,984,908 | * 11/1999 | Davis et al. | 604/282 |

OTHER PUBLICATIONS

Baxter Healthcare Corp. Research Medical Inc. Jan. 1, 1998 Catalogue pp. 2, 6, 7.
Bard Vascular Systems Division, C.R.Bard, Inc. Feb.1997 Catalogue pp. 3, 4, and two pages of illustrations of venous cannulae.
Murkin JM. CNS Complications in Cardiac Surgery: Retrograde Cerebral Perfusion, Pressure, Pulsatility, Temperature and pH Management During CPB. 21$^{st}$ Annual Meeting, Society of Cardiovascular Anesthesiologists 1999 Annual Meeting. 505–511.

* cited by examiner

Primary Examiner—Glenn K. Dawson
Assistant Examiner—Ann L. Lam
(74) Attorney, Agent, or Firm—David L. Marks

(57) ABSTRACT

A cavo-atrial cannula for removing blood from the body while performing heart surgery has at least two set of openings, a removable obturator, a curved tip, and a bend. The cavo-atrial cannula has the first openings located adjacent to the curved tip and the second openings on the side, opposite the bend. The cavo-atrial cannula contains various markings to indicate the correct positioning of the cavo-atrial cannula. The cavo-atrial cannula is inserted into the superior vena cava or inferior vena cava. The tip of the cavo-atrial cannula can lie in either the right atrium or the vena cava opposite from the insertion point. Because of the location of the second openings at the bend, blood from the head and upper body traveling through the superior vena cava or from the lower body traveling through the inferior vena cava can enter the lumen of the cavo-atrial cannula, thereby preventing the dangerous build up of blood upstream of the insertion point of the device. By inserting the cavo-atrial cannula into the vena cava and advancing it into the right atrium, one avoids the problems of trauma to the right atrium. A method for venous drainage having the steps of inserting a cavo-atrial cannula into a vena cava, advancing it into the right atrium, securing the cavo-atrial cannula, removing the removable obturator, and connecting the cavo-atrial cannula to tubing is also covered.

8 Claims, 3 Drawing Sheets

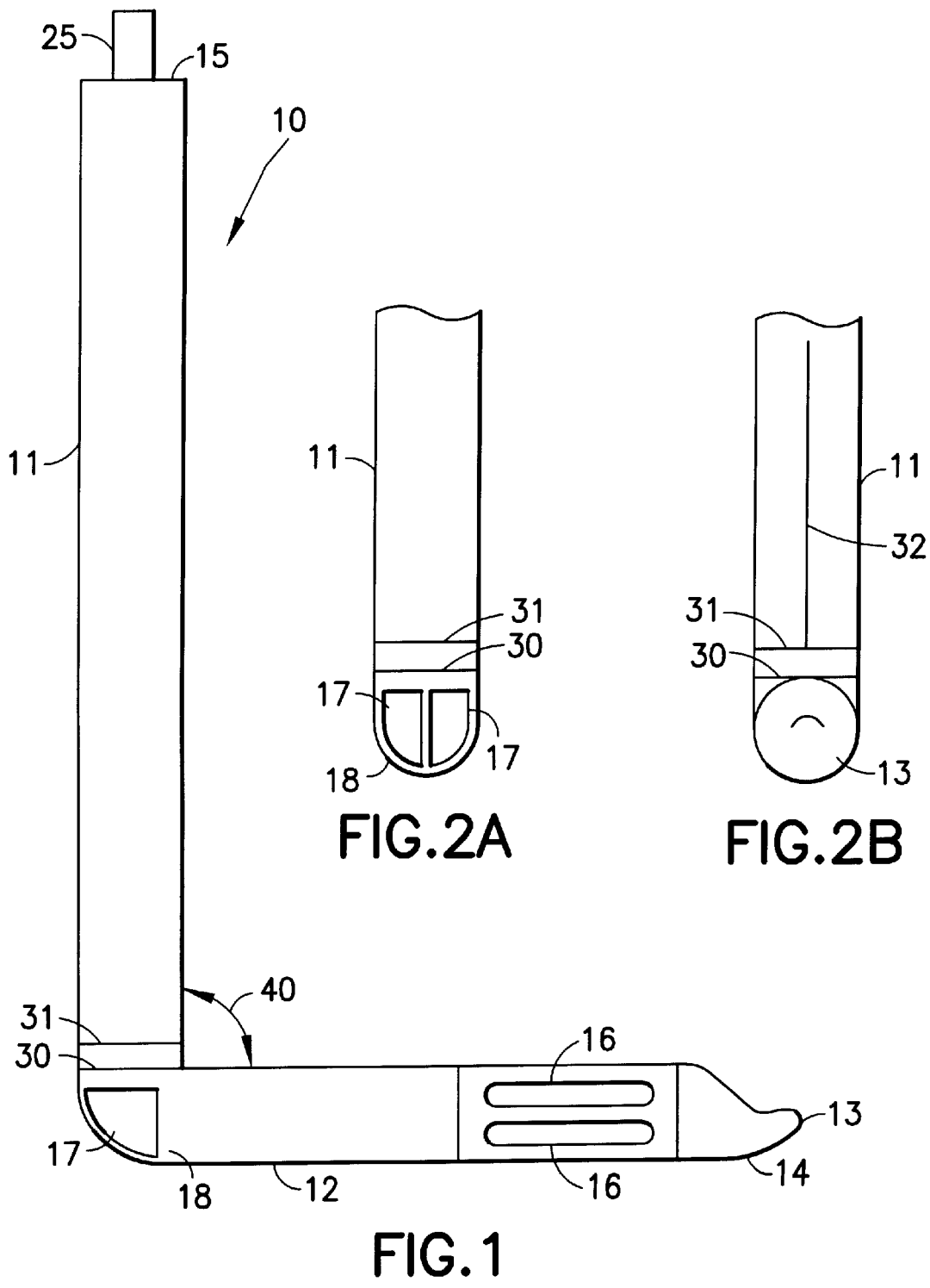

CAVO-ATRIAL CANNULA

CROSS-REFERENCE TO RELATED APPLICATIONS

None

STATEMENT REGARDING FEDERALLY SPONSORED RESEARCH OR DEVELOPMENT

None

REFERENCE TO MICROFICHE APPENDIX

N/A

BACKGROUND OF THE INVENTION

1. Field of the Invention

This invention relates to the field of heart surgery. More specifically, this invention relates to a cavo-atrial cannula, used to remove blood from the body while performing surgery on the heart, and the method of using such a device. This invention is a single cannula, introduced into the right atrium via the superior vena cava or inferior vena cava, thereby avoiding an incision in the right atrium.

2. Description of the Related Art

During cardiopulmonary bypass for heart surgery a mechanical device, a pump oxygenator, drains the patient's blood, oxygenates it, and returns it to the patient through tubing connected to cannulae placed in the patient's heart and aorta. Typically, drainage is accomplished by a single venous cannula, possessing two sets of openings, placed through an incision in the right atrium and secured in place by a pursestring-suture tourniquet applied along the edges of the atrial incision such that the cannula tip lies in the inferior vena cava. The set of openings at the cannula's terminus drain blood from the inferior vena cava, and the openings proximal to it drain the blood which has arrived from the superior vena cava and other lesser sources into the right atrium. An alternative method uses two venous cannulae, one directed into the superior vena cava and the other into the inferior vena cava. One or both of these cannulae are introduced through incision(s) in the right atrium.

The currently used venous cannulae and the methods by which they are placed in the heart present certain problems. The right atrium suffers significant damage not only from the incisions made to introduce the cannula(e) but also because of the right atrium's relative inaccessibility to the protective measures used to preserve heart tissue functional integrity during surgery. These protective measures consist primarily of drugs, such as cardioplegic solutions, infused into the blood supply of the heart tissue to arrest beating, as well as the constant topical application of ice-cold saline on the surface of the arrested heart. The method by which the cannulae are currently placed in the right atrium prevents the protective drugs from reaching the atrial tissue constrained in the tourniquet. Furthermore, the atrial tissue at the entry site of the cannula escapes the cold saline bath inasmuch as the atrial tissue is suspended upward out of the chest by the outward course of the cannulae toward the pump oxygenator. The functional consequences of direct injury to the atrial tissue as well as the sub-optimal access to the protection afforded to the rest of the heart include decreased strength of contraction and, perhaps more importantly, disordered atrial rhythm, e.g., atrial fibrillation, which can cause poor cardiac function, blood clots, and dangerously high heart rates. The drugs used to treat atrial fibrillation also have an array of potentially dangerous side-effects. The economic costs of atrial dysfunction reflect the price of the drugs used to treat it, longer hospital stays, and the additional hospital admissions for related complications.

Currently available cannulae can not be inserted into the vena cava for drainage of blood from the vena cava and right atrium for three reasons. First, most currently available cannulae have too narrow a diameter for adequate venous drainage and to maintain adequate flow of blood from the patient. Second, even if the diameter of the currently available cannulae were enlarged enough to maintain adequate flow of blood from the patient, the placement of such enlarged diameter cannulae in the superior vena cava would cause significant obstruction to blood flow from the head and upper body which normally courses through the superior vena cava into the right atrium. Similarly, enlarged diameter cannulae can not be inserted into the inferior vena cava because the placement of such cannulae in the inferior vena cava would cause significant obstruction to blood flow from the lower body which normally courses through the inferior vena cava into the right atrium. Third, currently available cannulae contain circumferential openings. If a circumferential opening lies just within the vena cava, then it would increase the risk of entraining air into the pump circuit, causing an "air lock" and obstruction to flow.

The placement of the openings in the currently available cannulae are not appropriate for effective drainage of the blood flowing down the superior vena cava when the cannulae are inserted through the superior vena cava nor for effective drainage of the blood flowing up the inferior vena cava when the cannulae are inserted through the inferior vena cava. Usage of currently available cannulae for drainage of blood through the superior vena cava would cause obstruction of the blood flow and could cause swelling of the brain, neurological dysfunction, and stroke. Obstruction of inferior vena cava blood flow could cause congestion and dysfunction of the abdominal organs.

BRIEF SUMMARY OF THE INVENTION

This invention overcomes all of the problems associated with the prior art. The heart may be effectively drained of blood during cardiopulmonary bypass without injuring the right atrium, thereby according the right atrium all the benefits of cardioprotective measures. The device and the method of its use accomplish these effects by placing a cannula into the right atrial cavity through an incision in the adjacent vena cava. No incision is made in the atrium. There is no pursestring-suture tourniquet in the atrial tissue. Thus, the atrium lies well within the chest, accessible to the cold saline bath.

The present invention contains a bend in the cannula because a cannula entering the vena cava from the usual opening in the patient's chest must make a roughly right-angle bend to proceed on to the right atrium.

The present invention also contains openings at a bend in the cannula. These openings face the direction of approach of the blood from the head and upper body if the invention is inserted into the superior vena cava or from the lower body if the invention is inserted into the inferior vena cava. Thus, the openings must be on the outer aspect of the bend in the cannula. Furthermore, the openings at the cannula's bend are not circumferential.

Therefore, in addition to openings at the terminus of the cannula to drain the right atrium, the device incorporates separate openings in the cannula, specifically positioned on the outer aspect of the bend in the cannula such that it would receive the blood from the head and upper body when inserted through the superior vena cava into the right atrium and from the torso and lower body when inserted through the inferior vena cava into the right atrium.

Furthermore, in order to prevent the massive loss of blood during insertion of the cannula into the vena cava in the form of blood entering the openings at the terminus and exiting through the second opening before it is seated in the vena cava, the device incorporates a removable obturator to block the second opening from within the cannula until the cannula is properly seated, at which time the obturator is withdrawn from the lumen of the cannula.

To maximize drainage of blood from the right atrium, the diameter of the distal portion of the cannula should not be substantially less than that of the cannula resting in the vena cava. Therefore, the invention provides for no narrowing of the cannula beyond the vena cava openings except a short curved taper at the tip to facilitate initial insertion into the vena cava.

The invention also pertains to the method of removing blood from the patient by insertion of the cavo-atrial cannula into the superior vena cava or inferior vena cava, advancing the cavo-atrial cannula into the right atrium, and connecting the cavo-atrial cannula to a device that pumps blood from the body.

BRIEF DESCRIPTION OF THE SEVERAL VIEWS OF THE DRAWINGS

FIG. 1 shows a side view of the invention according to the preferred embodiment.

FIG. 2A shows a back view of the invention according to the preferred embodiment.

FIG. 2B shows a front view of the invention according to the preferred embodiment.

DETAILED DESCRIPTION OF THE INVENTION

FIG. 1 illustrates the preferred embodiment of a cavo-atrial cannula, 10. A cavo-atrial cannula is a hollow tube containing an upper portion, 11, a middle portion, 12, and a closed terminus, 14. The closed terminus contains a curved tip, 13. At the end opposite the curved tip is the cavo-atrial cannula's open terminus, 15. The cavo-atrial cannula possesses, at a minimum, two sets of openings, a first openings, 16, and a second openings, 17. The first openings may be circumferential, but the second opening can not be circumferential. In the preferred embodiment, the cavo-atrial cannula also contains a bend, 18, located at the junction between the upper portion and middle portion.

Figure 3:
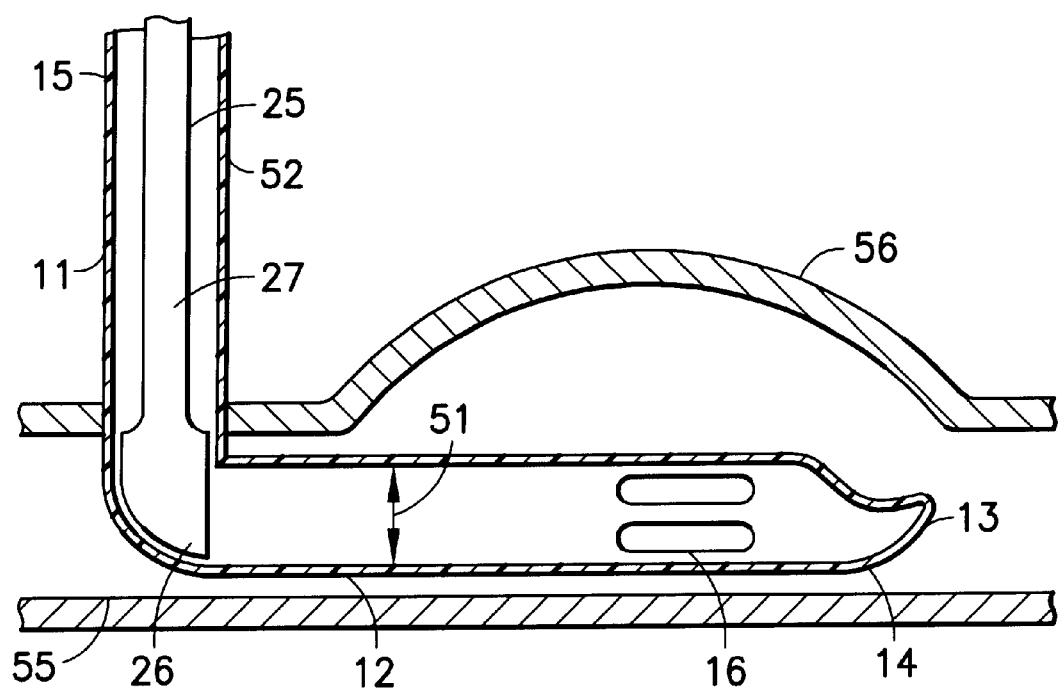
FIG. 3 shows a cut-away view of the invention according to the preferred embodiment.

As illustrated in FIG. 3, when used in adult patients, the interior diameter, 51, of the middle portion, 12, and upper portion, 11, is constant until the beginning of the closed terminus, 14. The interior diameter, 51, can range approximately between one to two centimeters which is sufficient width to permit blood to flow freely within the lumen of the cavo-atrial cannula, and to avoid sheer stress on the blood cells. The thickness of the walls, 52, of the cavo-atrial cannula do not add substantially to the overall diameter of the device. The overall diameter of the cavo-atrial cannula enables the invention to fit inside the patient's superior vena cava and/or inferior vena cava. For pediatric patients, the interior diameter, 51, and overall diameter will be smaller than when used for adult patients.

Referring to FIGS. 1, 2B, and 3, the curved tip, 13, has a gradual taper. Thus, the cavo-atrial cannula's overall diameter increases from the curved tip's terminus to the beginning of the middle portion, 12. The curved tip is curved in the plane and same direction as the bend, 18. The end of the curved tip terminates prior to it reaching beyond the overall diameter of the cavo-atrial cannula in order to minimize the tendency to snag tissue as the cavo-atrial cannula is advanced or withdrawn. The curved tip makes it easier for the user to insert the device into the patient's vena cava. The tapered, curved tip also helps the surgeon to negotiate the right angle of the vena cava with respect to the approach as he first inserts the cannula into the vena cava.

The first openings, 16, can be located anywhere between the closed terminus, 14, and a point in the middle portion located approximately three centimeters from the junction of the middle portion, 12, and the closed terminus. While the exact location can vary, the first openings should be located at a point where the interior diameter, 51, of the cavo-atrial cannula is large enough to permit blood to flow freely within the lumen of the cavo-atrial cannula, and to avoid sheer stress on the blood cells. When the cavo-atrial cannula is properly inserted, the first openings should be located inside the patient's right atrium. The first openings will be of sufficient size to permit the unobstructed flow of blood into the cannula and to minimize the disruption of red blood cells.

In FIG. 1, the bend, 18, is located at the junction of the middle portion, 12, and upper portion, 11. The angle of inclination, 40, of the bend can range from approximately twenty-five degrees (25°) to one-hundred eighty degrees (180°), depending on the physical properties of material used to make the cavo-atrial cannula. If the material is flexible and can bend without creating a closure of the lumen of the device, then the angle of inclination can be larger than one-hundred thirty-five degrees (135°). In the preferred embodiment, the angle of inclination ranges between forty-five degrees (45°) and one-hundred thirty-five degrees (135°).

In FIGS. 1 and 2A, the second openings, 17, of the cavo-atrial cannula is located at the junction of the upper portion, 11, and the middle portion, 12, on the outer side of the bend, 18. When the cavo-atrial cannula is properly inserted into the vena cava, the second openings is located so that blood from the vena cava can flow into the cavo-atrial cannula. If the second openings was absent the cavo-atrial cannula would obstruct the flow of blood from the head to the heart when the invention is inserted into the superior vena cava or from the lower body to the heart when the invention is inserted into the inferior vena cava. The distance from the curved tip, 13, to the second openings, 17, can range from approximately five centimeters to approximately ten centimeters.

The first openings, 16, and the second openings, 17, can be a plurality of holes or slits adjacent to each other in the walls of the cavo-atrial cannula. They may run laterally or longitudinally. It is recommended that the walls of the cavo-atrial cannula proximal to and surrounding the openings be of a stiffer, stronger material than the rest of the walls of the cavo-atrial cannula for increased support. The increased support is recommended but not vital.

The distance between the first openings and the second openings can range from approximately five to ten centimeters, the distance between a convenient insertion site on the vena cava and the middle of the right atrium in an average sized heart. The length of the upper portion can be approximately twenty centimeters.

The cavo-atrial cannula, 10, can be made of any material that is approved by the Food and Drug Administration for these types of devices. The material should be flexible yet not able to bend or kink so that the flow of blood will not be obstructed. Use of a polyvinylchloride reinforced with an intramural spiral wire is commendable.

In FIGS. 1 and 3, the cavo-atrial cannula has a removable obturator, 25, located inside the lumen of the invention, extending from the second openings, 17, through the open terminus, 15. The obturator occludes the second openings while the cavo-atrial cannula is being inserted into the patient. The obturator prevents blood which enters the lumen of the cavo-atrial cannula via the first openings, 16, from leaving the lumen of the invention through the second openings, 17, prior to the proper seating of the cavo-atrial cannula within the vena cava. Without the obturator, blood may exit the cavo-atrial cannula inappropriately, causing excessive bleeding, blood loss, and possibly death. The obturator, 25, may be made from plastic or any other appropriate material. The obturator has an occluding portion, 26, and non-occluding portion, 27. The occluding portion covers the second openings, 17, and extends above the second openings for some distance. The diameter of the occluding portion is identical to or slightly smaller than the interior diameter, 51, of the cavo-atrial cannula so that the occluding section fits snugly inside the lumen of the invention and prevents blood from entering or exiting the cannula through the second openings, 17. The diameter of the non-occluding portion, 27, of the obturator can be less than the interior diameter, 51, of the cavo-atrial cannula so as to reduce friction during withdrawal and insertion of the obturator, 25. When properly seated, the obturator terminates at or just beyond the bend, 18, and blocks completely the second openings, 17. The obturator may be solid or hollow.

After the cavo-atrial cannula is properly inserted into the vena cava and is secured into place with a pursestring tourniquet, one slides the obturator, 25, out through the open terminus, 15, thereby uncovering the second openings, 17. Then, blood from the vena cava can enter the lumen of the cavo-atrial cannula through the second openings. When the cavo-atrial cannula is used properly, the open terminus, 15, remains outside the vena cava. After removal of the obturator, 25, one connects the open terminus, 15, of the cavo-atrial cannula to tubing that carries the blood to a pump oxygenator. The patient's blood will not exit the cavo-atrial cannula through the open terminus, 15, prior to connecting the cavo-atrial cannula to the pump oxygenator because the hydrostatic pressure within the patient's vena cava lacks enough force to raise the blood to top of the cavo-atrial cannula and out the open terminus. However, one must take care to prevent the invention from moving or otherwise allowing the open terminus of the cavo-atrial cannula to drop.

As shown in FIGS. 1, 2A and 2B, the cavo-atrial cannula has a plurality of markings on the upper portion, 11. The safe mark, 30, indicates the lowest level at which one can safely tighten and secure a pursestring suture. The safe mark is located approximately five millimeters above the top of the second openings, 17, and designates the point beyond which the cavo-atrial cannula should not be withdrawn from the patient's vein because of the danger of air entrainment. Air entrainment can occur if, after the cavo-atrial cannula is connected to a oxygenator pump, air enters the lumen of the cavo-atrial cannula through the second openings and causes an air-lock. The safe mark ensures the proper depth of insertion of the cavo-atrial cannula. The reference mark, 31, is located approximately five millimeters above the safe mark. The reference mark serves as a reference to warn that the last extent of safe withdrawal of the cavo-atrial cannula during seating is nearby. The safe mark and reference mark extend around the upper portion, 11, perpendicular to the direction of flow of blood through the cavo-atrial cannula.

In FIGS. 1 and 2B, the rotation mark, 32, runs on the exterior of the cavo-atrial cannula, on the side containing the angle of inclination, 40, and opposite the location of the second openings, 17. It begins on the middle portion, 12, and terminates on the upper portion, 11, above the safe mark, 30. The rotation mark, 32, assists in identifying the axial rotation of the second openings, 17, particularly in those embodiments of the invention with a angle of inclination greater than 90°.

FIG. 3 illustrates the relative placement of the cavo-atrial cannula when inserted into a vena cava, 55, and advanced into the right atrium, 56. The obturator, 25, is not removed until the cavo-atrial cannula is detachably, securely fastened into proper position by placement of a Rummel tourniquet with a pursestring suture. The suture and tourniquet are placed at the safe mark, 30, or higher than the safe mark (see FIG. 1).

Figure 4:
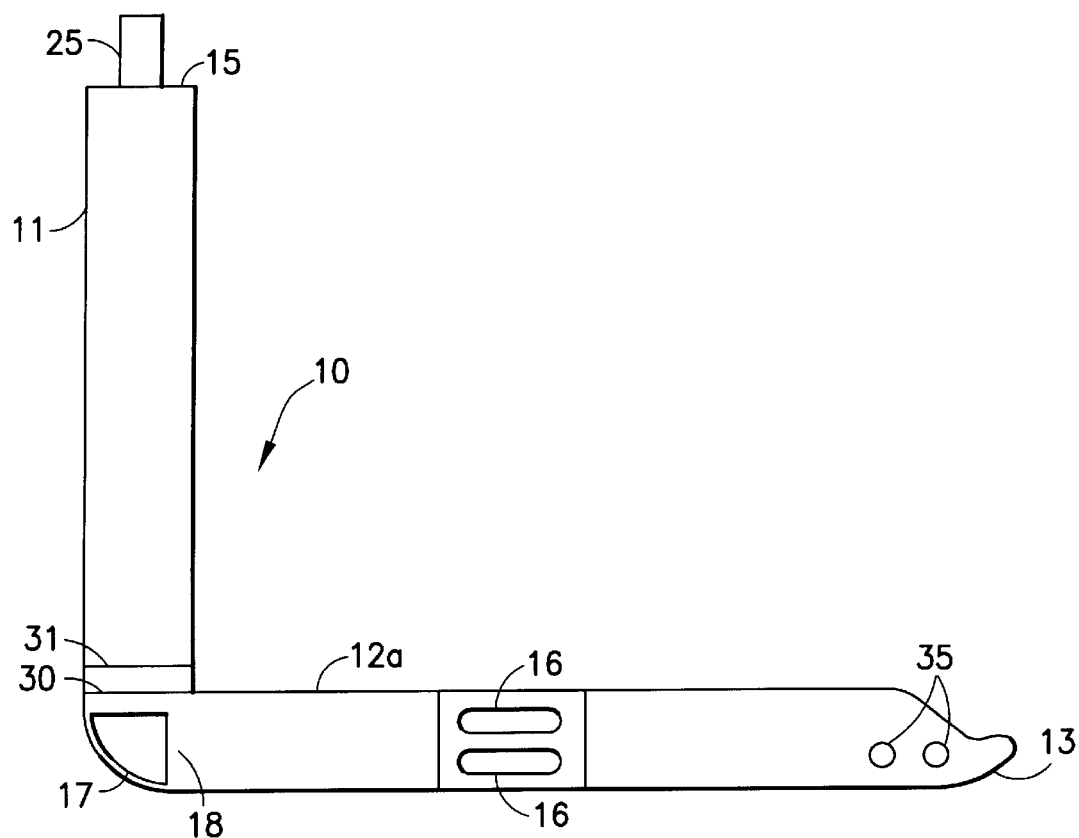
FIG. 4 shows a side view of an alternative embodiment of the invention.

As illustrated in FIG. 4, in one alternative embodiment, the cavo-atrial cannula has three sets of openings. This alternative embodiment differs from the preferred embodiment by having an extended middle portion, 12a, and another set of openings, the third openings, 35. The third openings, 35, is located in or just prior to the beginning of the curved tip, 13. The extended middle portion allows the curved tip, 13, and third openings, 35, to lie in the vena cava opposite the site of insertion. The third openings, 35, when the cavo-atrial cannula is properly inserted into the superior vena cava, is located in the inferior vena cava, and thus can drain blood from the inferior vena cava. The extended middle portion, 12a, is extended approximately eight centimeters in length. In this alternative embodiment, the first openings, 16, and the second openings, 17, are located in the same positions with respect to each other on the cavo-atrial cannula as in the preferred embodiment containing two sets of openings.

The method of heart surgery using the cavo-atrial cannula differs from current surgical techniques. Instead of making a hole in the right atrium and inserting the cavo-atrial cannula through the right atrium into the inferior vena cava, one makes a hole in the superior vena cava and inserts the cavo-atrial cannula into the superior vena cava. One then advances the cavo-atrial cannula down the superior vena cava to the right atrium. (See FIG. 3) The curved tip should either rest within the right atrium or the inferior vena cava, depending on which embodiment of the device one uses. The cavo-atrial cannula should be inserted such that the second openings, 17, is located inside the patient's superior vena cava and pointed toward the patient's head. In such a manner, one drains the patient's blood from both the superior vena cava and right atrium, or the superior vena cava, right atrium, and inferior vena cava, depending on which embodiment of the cavo-atrial cannula is used. The curved tip assists in the insertion of the cavo-atrial cannula into the patient's vein.

Alternatively, one makes a hole in the patient's inferior vena cava, and insert the cavo-atrial cannula so that the curved tip either rests within the right atrium or the superior vena cava, depending on which embodiment of the cavo-atrial cannula one uses. (See FIG. 3) One should use caution when using this alternative method because the extent of the inferior vena cava in the chest is quite short. However, in this method, one drains the blood from the right atrium and the inferior vena cava or the right atrium, inferior vena cava, and superior vena cava, depending on which embodiment of the cavo-atrial cannula is used.

One uses the safe mark, 30, and reference mark, 31, on the upper portion, 11 to make sure that the cavo-atrial cannula is inserted to the proper depth. One uses the rotation mark, 32, to make sure that the cavo-atrial cannula is in the proper orientation.

One secures the cavo-atrial cannula with a variety of methods known in the field. A preferred method is using a Rummel tourniquet with a pursestring suture to secure the cavo-atrial cannula to the superior vena cava or inferior vena cava.

After the cavo-atrial cannula is inserted into the patient's vena cava and properly secured, one removes the obturator, 25, by withdrawing the obturator through the open terminus, 15. Then, one attaches the cavo-atrial cannula to any tubing which takes blood to a pump oxygenator or any other instrument. Gravity drainage or augmented suction drainage is possible with this device. Other instruments to which the cavo-atrial cannula can be attached may utilize other methods for the draining of blood. Blood is returned to the patient's body via tubing and a cannula inserted into the aorta or other artery.

While using the cavo-atrial cannula, cardioplegic solutions can be perfused into the heart's blood supply and ice-cold saline can be applied topically to the heart, if the surgeon so chooses.

When one has completed the surgical tasks that required the diversion of the patient's blood to a pump oxygenator, one weans the heart from the pump oxygenator and removes the to cavo-atrial cannula. Then one closes the hole in the patient's superior vena cava or inferior vena cava using sutures.

Although the present invention has been described and illustrated in detail, it is clearly understood that the same is by way of illustration and example and is not to be taken by way of limitation, the spirit and scope of the present invention being limited only by terms of the appended claims.

I claim:

1. A cavo-atrial cannula comprising:
    a cannula having an open terminus and a closed terminus;
    a bend;
    a first openings wherein said first openings are located adjacent to said closed terminus;
    a second openings wherein said second openings are located on the side of said cannula opposite said bend;
    a removable obturator capable of occluding said second openings;
    a safe mark located between said second openings and said open terminus wherein said safe mark designates the point beyond which said cavo-atrial cannula should not be withdrawn from a vein while in use in order to prevent air entrapment within said cavo-atrial cannula;
    and a reference mark located between said safe mark and said open terminus wherein said reference mark warns that said safe mark is nearby.

2. A cavo-atrial cannula of claim 1 further comprising:
    wherein said bend has an angle of inclination between forty-five degrees and one-hundred thirty-five degrees.

3. A cavo-atrial cannula of claim 2 further comprising:
    said closed terminus further comprises a curved tip.

4. A cavo-atrial cannula of claim 3 further comprising:
    a rotation mark located on the side of said cannula opposite said second openings, along said bend and extending above said bend wherein said rotation mark identifies the axial rotation of said second openings.

5. A cavo-atrial cannula comprising:
    a cannula having an open terminus and a closed terminus;
    a bend;
    a first openings wherein said first openings are located adjacent to said closed terminus;
    a second openings wherein said second openings are located on the side of said cannula opposite said bend;
    a third openings where said third openings are located between said first openings and said second openings;
    a removable obturator capable of occluding said second openings;
    a safe mark located between said second openings and said open terminus wherein said safe mark designates the point beyond which said cavo-atrial cannula should not be withdrawn from a vein while in use in order to prevent air entrapment within said cavo-atrial cannula;
    and a reference mark located between said safe mark and said open terminus wherein said reference mark warns that said safe mark is nearby.

6. A cavo-atrial cannula of claim 5 further comprising:
    wherein said bend has an angle of inclination between forty-five degrees and one-hundred thirty-five degrees.

7. A cavo-atrial cannula of claim 6 further comprising:
    said closed terminus further comprises a curved tip.

8. A cavo-atrial cannula of claim 7 further comprising:
    a rotation mark located on the side of said cannula opposite said second openings, along said bend and extending above said bend wherein said rotation mark identifies the axial rotation of said second openings.

* * * * *